(12) United States Patent
Nathanson

(10) Patent No.: US 9,398,775 B2
(45) Date of Patent: Jul. 26, 2016

(54) DIETARY MEASUREMENT SYSTEM AND METHOD OF CORRELATING DIETARY CONTENTS INFORMATION TO A DEFINED VOLUME

(71) Applicant: George Alexander Nathanson, Santa Fe, CA (US)

(72) Inventor: George Alexander Nathanson, Santa Fe, CA (US)

( * ) Notice: Subject to any disclaimer, the term of this patent is extended or adjusted under 35 U.S.C. 154(b) by 417 days.

(21) Appl. No.: 13/789,096

(22) Filed: Mar. 7, 2013

(65) Prior Publication Data

US 2014/0257749 A1    Sep. 11, 2014

(51) Int. Cl.
| | |
|---|---|
| *G06F 19/00* | (2011.01) |
| *A23L 1/29* | (2006.01) |
| *G01F 22/00* | (2006.01) |
| *G01N 33/02* | (2006.01) |
| *G01F 19/00* | (2006.01) |

(52) U.S. Cl.
CPC .................. *A23L 1/293* (2013.01); *G01F 19/00* (2013.01); *G01F 22/00* (2013.01); *G01N 33/02* (2013.01)

(58) Field of Classification Search
CPC ................ A61K 2300/00; G01N 2035/00326; G01N 2035/00495
USPC .................. 702/51, 52, 47, 182–185
See application file for complete search history.

(56) References Cited

U.S. PATENT DOCUMENTS

| | | | |
|---|---|---|---|
| 923,618 | A | 6/1909 | Blizard |
| 2,256,865 | A | 9/1941 | Gilbert |
| 2,479,007 | A | 8/1949 | Gruben |
| 2,551,002 | A | 5/1951 | Jennings |
| 2,839,928 | A | 6/1958 | Fohrman |
| 4,154,109 | A | 5/1979 | Kelson |
| 4,388,839 | A | 6/1983 | Benisti |
| 4,981,041 | A | 1/1991 | Merkle |
| 5,402,679 | A | 4/1995 | Vogel |
| D361,532 | S | 8/1995 | North, III et al. |
| D365,987 | S | 1/1996 | Willard |
| D366,840 | S | 2/1996 | Schagerstrom et al. |
| D368,865 | S | 4/1996 | Weterrings |
| D369,304 | S | 4/1996 | Weterrings |
| 6,026,685 | A | 2/2000 | Weterrings et al. |
| D451,827 | S | 12/2001 | Winters |

(Continued)

FOREIGN PATENT DOCUMENTS

| | | |
|---|---|---|
| CN | 2015551054 U | 8/2010 |
| GB | 2479588 | 10/2011 |
| JP | 10078344 | 3/1998 |

*Primary Examiner* — Edward Raymond
(74) *Attorney, Agent, or Firm* — Franklin & Associates International Inc; Matthew F. Lambrinos

(57) ABSTRACT

A dietary measurement system and a method of correlating dietary information to a defined volume of a measuring device are provided to reduce the effort and time necessary to keep track of the nutritional intake. The dietary measurement system comprises at least a measuring device adapted to accommodate food having multiple measurement indicators representing defined volumes, a nutrition database comprising dietary contents information for food and a mapping device. The mapping device comprises an input interface for receiving food selection information and a mapping processor, connected with said input interface and said nutrition database, said mapping processor being adapted to generate dietary correlation data from said dietary contents information, said dietary correlation data providing a reference between one of said measurement indicators of said measuring device and a given dietary contents level for food according to said food selection information.

14 Claims, 13 Drawing Sheets

(56) References Cited

U.S. PATENT DOCUMENTS

| | | |
|---|---|---|
| D451,828 S | 12/2001 | McGuyer |
| 6,948,366 B2 | 9/2005 | Bang |
| D519,040 S | 4/2006 | Bertulis |
| 7,340,953 B2 | 3/2008 | Green et al. |
| 7,658,106 B2 | 2/2010 | Price et al. |
| D643,747 S | 8/2011 | Rye |
| 8,256,130 B2 | 9/2012 | Jantz |
| 2005/0025864 A1 | 2/2005 | Gordon |
| 2005/0226970 A1 | 10/2005 | Gordon |
| 2006/0240152 A1 | 10/2006 | Krawzsenek |
| 2007/0157576 A1* | 7/2007 | Till .................. B65C 9/46 53/471 |
| 2009/0012433 A1* | 1/2009 | Fernstrom ........... A61B 5/1112 600/593 |
| 2010/0086653 A1 | 4/2010 | Fedele et al. |

* cited by examiner

DIETARY MEASUREMENT SYSTEM AND METHOD OF CORRELATING DIETARY CONTENTS INFORMATION TO A DEFINED VOLUME

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

TECHNICAL FIELD

The present invention relates to the field of nutritional science and, more particularly but not exclusively, to dietary measurement systems and methods.

BACKGROUND

During recent years, large parts of the society became aware of the health benefits of a well-balanced lifestyle including sufficient physical activity and a healthy nutrition. Individuals not only tend to eat more healthy foods, but also like to keep track of the intake of nutrients, vitamins, fat, fiber, sodium, cholesterol, carbohydrate, protein and also daily calorie intake. Keeping track of the daily intake may be particularly important when keeping a diet plan, which has become more popular in the recent past.

Dieting requires some administrative effort so that it may be difficult to keep the diet over an elongated time period as would typically be necessary. Accordingly, a system and a method is needed to facilitate controlling diet.

SUMMARY

The following summary of the present invention is provided to facilitate an understanding of some of the innovative features unique to the present invention and is not intended to be a full description. A full appreciation of the various aspects of the invention can be gained by taking the entire specification, claims, drawings, and abstract as a whole.

According to one aspect of the present invention, a dietary measurement system is provided. The system can comprise at least a measuring device, a nutrition database and a mapping device.

In one non-limiting example, the measuring device is adapted to accommodate food and has multiple measurement indicators representing defined volumes. The nutrition database can comprise dietary contents information for food. The mapping device can comprise an input interface for receiving food selection information and a mapping processor, connected with the input interface and the nutrition database. In one non-limiting example, the mapping processor adapted to generate dietary correlation data from the dietary contents information, the dietary correlation data providing a reference between one of the measurement indicators of the measuring device and a given dietary contents level for food according to the food selection information.

In another aspect, a method of correlating dietary information to a defined volume with a measuring device adapted to accommodate food having multiple measurement indicators is provided. According to the present method aspect, food selection information is received, dietary contents information according the food selection information is received and dietary correlation data is generated from the dietary contents information. The dietary correlation data provides a reference between one of the measurement indicators and a given dietary contents level for food according to the food selection information.

The term "dietary contents level" as referred to herein corresponds to a defined level of dietary contents information, i.e. content of nutrients such as vitamins, protein, fat, carbohydrate, minerals, sodium, cholesterol, content of calories and/or any other suitable nutritional parameter for food that is of interest to the user. The respective dietary contents level may be pre-set or entered by a user as will be explained in more detail in the following.

The basic idea of one or more embodiments of the present invention is to allow correlation of a defined volume, i.e. corresponding to one of the multiple measurement indicators of the measuring device with a dietary contents level for selected food, so that a user may determine the amount of food corresponding to the desired dietary contents level easily, i.e. reducing the effort and time necessary to keep track of the nutritional intake.

One or more embodiments are based on the present inventors recognition that a relation exists between the volume of a specific food item and dietary contents information, such as e.g. calorie content. In one example, the dietary system and method allows the user to e.g. determine the volume and thus the amount of a specified food, which corresponds to a "snack size" of 100 cal.

In the following explanation of the present invention according to the embodiments described, the terms "connected to" or "connected with" are used to indicate a data connection/transmission link between at least to components. Such connection may be direct between the respective elements or indirect, i.e. over intermediate components.

As discussed above, the dietary measurement system according to a first aspect of the invention comprises the measuring device, the nutrition database and the mapping device. The measuring device may be of any suitable type to accommodate food, e.g. a suitable container, cup, bowl, plate or measuring spoon. The measuring device comprises multiple measurement indicators, representing defined volumes, where the volume associated with one of the measurement indicators differs from the respective volumes, associated with the other measurement indicators.

The measurement indicators are suitably adapted to allow a user to determine whether a volume of food in the measuring device corresponds to the respective measurement indicator. For example, the measurement indicators may comprise (colored) lines, numbers and/or other suitable markings. The measurement indicators may be formed integrally with a measurement compartment of the measuring device or be formed as a separate component. In case the measuring device comprises an at least partly transparent measurement compartment, the measurement indicators are for example visible from the outside of the compartment for easy operation and for example are arranged on the outside surface of the measurement compartment. The multiple measurement indicators may be evenly spaced from each other in an embodiment of the present aspect of the invention.

Certainly, the measuring device may in some embodiments comprise further components or may be formed integrally with the mapping device or other components of the inventive system, as will be explained in more detail in the following.

According to the present aspect of the invention and as mentioned in the preceding, the mapping device comprises the input interface and the mapping processor. The before mentioned components may be arranged integrally, such as in a housing or may be a separated from each other. In the latter case the components may be connected using a suitable telecommunications protocol and network, such as the Internet.

The input interface of the mapping processor may be suitably adapted to receive at least the food selection information, which in the present context is understood to comprise a selection of one or more foods/food items. In general, a user may enter the food selection information. Accordingly, the input interface may be a user interface for user entry of the food selection information. However, in other non-limiting examples, the food selection information is received by the input interface from a memory or other input device, e.g. storing a selection entered by a user before. Thus, the input interface may also be a network interface, connecting the mapping device to a computer network and/or to the memory device mentioned before. The input interface may be adapted to receive further information, such as the at least one dietary contents level, e.g. from user input.

The nutrition database according to the present aspect of the invention comprises dietary contents information for food, as mentioned above. The dietary contents information allows the mapping processor to generate dietary correlation data, i.e. to provide a reference between one of the measurement indicators and the given dietary contents level. Therefore, the dietary contents information in general allows the mapping processor to correlate information on nutritional contents to a defined volume, such as caloric content of a certain food to the defined volume represented by one of the measurement indicators. In one non-limiting example, the dietary correlation data may comprise a reference to an intermediate volume between two subsequent measurement indicators, e.g. in a decimal representation. For example, in case of two measurement indicators labeled "1" and "2", the dietary correlation data may comprise a reference to "1.5" or "1⅔", i.e. to a volume between the volume associated with measurement indicator 1 and measurement indicator 2.

While it may be possible that the dietary contents information comprises a reference to a unit of measurement, e.g. caloric content of food per cubic millimeters or inch, such reference may be omitted as long as the mapping processor is enabled to generate the dietary correlation data, i.e. reference one of the measurement indicators to the given dietary contents level.

Certainly, the nutrition database may comprise dietary contents information for multiple foods. Additionally or alternatively, the dietary contents information may comprise more than one of contents of nutrients such as vitamins, protein, fat, carbohydrate, minerals, sodium, cholesterol, content of calories and/or any other suitable nutritional parameter for food.

The nutrition database may comprise a suitable memory to store the dietary contents information, such as solid state memory (RAM, ROM, Flash memory, USB memory), hard drive storage, optical storage (CDs, DVDs, Blurays), magnetic storage or other suitable type of volatile or non-volatile memory. The nutrition database may in one embodiment be formed integrated with the mapping device or may be provided separate there from.

The mapping processor according to the present aspect of the invention is connected with the input interface and the nutrition database to generate the dietary correlation data. The mapping processor may be of any suitable type to generate the data and may comprise a microcontroller, microprocessor and/or a computer device, each of which are provided with a suitable programming. Certainly, the mapping processor may be configured to determine the dietary correlation data for multiple foods.

Once the dietary correlation data is generated, the mapping processor may be adapted to present the data to the user, e.g. over a connected output device, so that the user may then measure the desired amount of food using the measuring device.

In one embodiment, the user may utilize the system by selecting one or more food items together with the desired dietary contents level, such as calorie content. The input interface accordingly receives food selection information and the set dietary contents level, both of which are transmitted to the mapping processor. The mapping processor queries the nutrition database with the selected foods and receives back dietary contents information for the selected foods. The mapping processor generates dietary correlation data, providing a reference between one of the measurement indicators and the dietary contents level set. The dietary correlation data is then presented to the user. A measurement of the food according to the desired dietary contents level is then easily possible by filling the volume of the measuring device with food, which corresponds to the measurement indicator according to the dietary correlation data.

According to another embodiment of the invention, the input interface is adapted to receive at least a lower dietary information level and an upper dietary information level. Further, the mapping processor in this embodiment may be adapted to generate dietary correlation data for both of the dietary information levels.

The present embodiment provides an enhanced measurement and further simplifies the operation for a user. For example, in some applications the user may wish to receive dietary correlation data for a "snack size" of 100 calories and a larger serving of 140 calories. The present embodiment allows to easily receive the dietary correlation data corresponding to both serving sizes simultaneously.

According to a further embodiment, the dietary contents information comprises at least caloric content information for one or more foods. This is particularly useful since most diet plans are based on the daily caloric intake. The dietary contents level may additionally or alternatively comprise a caloric content level.

In one embodiment, the mapping device further comprises an output device, connected with the mapping processor. The output device receives at least the generated dietary correlation data and may be adapted to provide the data to a user. The output device may e.g. be a printing device or a network interface.

In a further example, the output device comprises a display unit to display the dietary correlation data to a user. The present embodiment further facilitates the measurement for the user.

The display unit may be formed integrally with the mapping device, e.g. in a common housing with the input interface and/or the mapping processor. Alternatively, the display unit may be provided spaced from the mapping processor and/or input interface. In this case, the display unit may be connectable to the mapping device by a suitable wired or wireless communication connection, such as USB, LAN, WIFI, Bluetooth or near-field communication.

Furthermore, it may be possible that the display unit is integrated with one or more further components of the system, such as the measuring device. In the latter case, the measuring device may have a receptacle for a removable connection of the display device, which receptacle being arranged so that the display device is separated from the food. The display unit may e.g. be of LCD, LED or seven-segment type. Alternatively, the display unit may be integrated with a further device such as a smart phone, tablet computer, laptop, desktop computer or another type of computing device.

In another embodiment, the mapping device comprises a housing, the housing having a connecting portion for fixation of the mapping device to the measuring device. The housing may be of any suitable type to accommodate at least the input interface, nutrition database, mapping processor and/or the before mentioned display unit. The connecting portion should be adapted for engagement with the measuring device, e.g. with a corresponding second connecting portion of the measuring device.

The present embodiment provides a very compact setup, which may be easily used and stored in an area of food preparation, e.g. on a kitchen countertop.

According to a further embodiment of the invention, the measuring device comprises a measuring compartment to accommodate food and a receptacle for receiving a dietary correlation label. The receptacle is arranged so that the dietary correlation label is separated from the food.

In the context of the present embodiment, the dietary correlation label provides the generated dietary correlation information to the user, i.e. in a user-readable format. For example, the dietary correlation label may be a computer printout, a user-inscribable sheet, a black board, a magnetic drawing screen or any other suitable type of label.

In particular in the case of the present embodiment, the mapping device and/or processor may be further adapted to generate a label printing template comprising the generated dietary correlation data to allow printing of the dietary correlation label.

In the present context, the label printing template comprises data, allowing a printing device to print the dietary correlation label, i.e. a user-readable representation of the dietary correlation data.

The label printing template may be send by the mapping processor to a suitable printing service or printing device for the printing of the label. Alternatively or additionally, the mapping processor may be configured to send the label printing template to the user, e.g. by e-mail, and/or to provide the label printing template on the Internet for user download. The user may then easily print the dietary correlation label on his printing device.

In an alternative or additional embodiment, the output device comprises a printing device, connected with the mapping processor to provide the dietary correlation label from the label printing template. The printing device may be of any suitable type, for example laser, inkjet or thermal transfer type.

As discussed in the preceding, the measurement device may be of any suitable type to accommodate food and may have a measuring compartment. According to a further embodiment of the present aspect of the invention, the measuring compartment is a volume adjustable compartment.

For example, the measuring compartment may have a fixed portion and at least one displaceable wall having a handle portion. In addition, the wall and/or handle may be adapted to engage with multiple recesses of the fixed portion during displacement, where each recess corresponds to one of the measurement indicators, so that the volume of the measuring compartment upon engagement corresponds to the volume, associated with the respective measurement indicator.

In a further exemplary additional or alternative embodiment, the measuring device comprises an outer and an inner cylinder, where the inner cylinder may be slidable arranged in the outer cylinder.

Both cylinders may be made from a suitable material, for example from metal, glass, porcelain, stoneware or a polymer such as acrylic glass. Certainly, the inner cylinder should at least partly have a smaller diameter than the outer cylinder to provide the mentioned slidable arrangement. One or both of the cylinders may comprise a seal and/or a guidance device. The cylinders may be formed at least partly transparent to further facilitate using the system. In one embodiment, the measurement indicators are provided on the outer cylinder. In another alternative or additional embodiment, one or more of the cylinders are made from a durable material for cleaning in a dishwasher and/or are made from a food safe material.

According to a further embodiment, the inner cylinder comprises a sealing endplate on a first axial end of the inner cylinder, so that the measuring compartment is formed between the outer cylinder and the endplate of the inner cylinder. This embodiment provides a space-saving storage of the measuring device when not in use.

In another alternative or additional embodiment, the mentioned receptacle for the dietary information label is formed in the inner cylinder. Accordingly, the label is kept separated from the food in the measuring compartment.

In one embodiment, the inner wall of the inner cylinder and/or the sealing endplate forms the receptacle. A second detachable endplate may additionally or alternatively be provided at a second axial end of the inner cylinder to keep the label from unintended ejection but allow an easy insertion of the dietary correlation label into the receptacle. The second endplate may be formed as a stand for the measuring device and/or a handle for user operation.

A second aspect of the present invention relates to a measuring device adapted to accommodate food. The measuring device comprises at least a measuring compartment to accommodate food having multiple measurement indicators representing defined volumes and a receptacle for receiving a dietary correlation label, the receptacle being arranged so that the dietary correlation label is separated from the food.

The measuring device according to the present aspect facilitates the measurement of defined volumes of food corresponding to a given dietary contents level. The measuring device may further be adapted according to one or more embodiments discussed in the preceding with reference to the first aspect of the present invention.

Another aspect of the present invention relates to a mapping device for use in a dietary measurement system. The mapping device comprises an input interface for receiving food selection information and a mapping processor, connectable to a nutrition database comprising dietary contents information for food. The mapping processor being adapted to generate dietary correlation data from the dietary contents information, the dietary correlation data providing a reference between at least one measurement indicator of a measuring device having multiple measurement indicators and a given dietary contents level for food according to the food selection information.

The mapping device may certainly be adapted according to one or more embodiments discussed in the preceding with reference to the first aspect of the present invention.

According to another aspect of the present invention, a method of correlating dietary information to a defined volume of a measuring device adapted to accommodate food having multiple measurement indicators is provided. In the method of the present aspect, food selection information is received, dietary contents information according the food selection information is received and dietary correlation data is generated from the dietary contents information, the dietary correlation data providing a reference between one of the measurement indicators and a given dietary contents level for food according to the food selection information.

In one embodiment of the present aspect of the invention, a label printing template is generated, the label printing template comprising the dietary correlation data to allow printing of a dietary correlation label.

A computer program or module may be provided to enable a processor to carry out the method discussed above. The computer program may be contained on a computer readable medium, such as a solid state, magnetic or optical storage device.

These and other aspects of the invention will be apparent from and elucidated with reference to the embodiments described hereinafter.

DETAILED DESCRIPTION OF PREFERRED EMBODIMENTS

Figure 1:
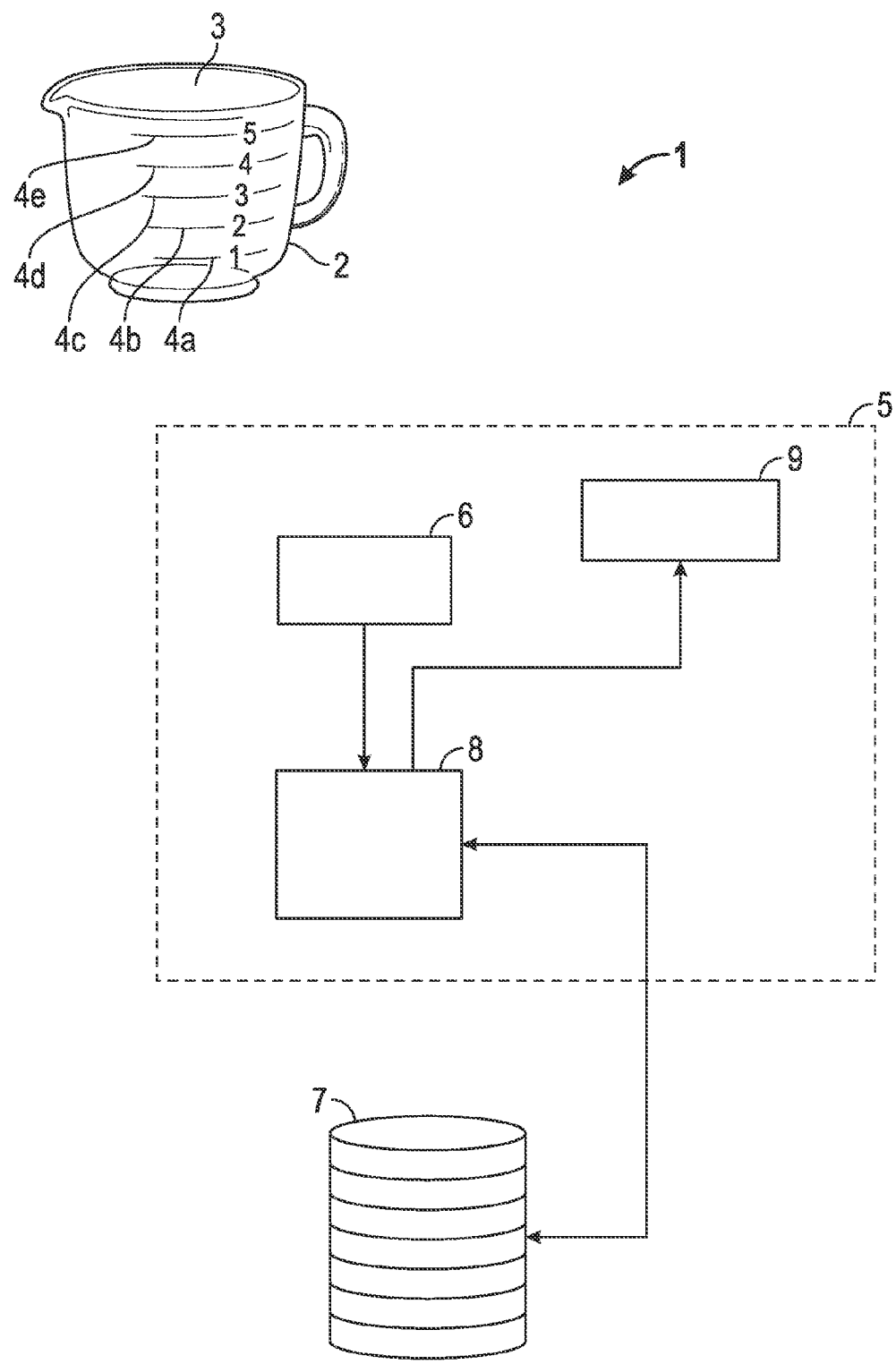
FIG. 1 shows an embodiment of a dietary measurement system according to a first aspect of the invention in a schematic block diagram.

Technical features described in this application can be used to construct various embodiments dietary measurement systems and methods, according to embodiments described herein.

It has been identified that keeping track of ones daily nutritional intake may be difficult. Some of this difficulty may be attributed to the challenge of proper measuring. Most individuals find using a scale to weight serving sizes cumbersome. Furthermore, measuring specific target values, i.e. other than those contained in a serving size typically requires utilizing arithmetic, which may further complicate and lengthen the process.

In one approach, a dietary system comprises a mapping device capable of accessing a nutrition database of dietary contents information for food. The mapping device has an input interface for receiving food selection information and a mapping processor, connectable with the input interface and the nutrition database. The mapping processor is adapted to generate dietary correlation data from the dietary contents information for use with a measuring device, the dietary correlation data representing a reference between one or more measurement indicators representing defined volumes of the measuring device and a given dietary contents level for food according to the food selection information.

By configuring the mapping device to generate from the dietary contents information dietary correlation data for use with the measuring device and that represents a reference between the measurement indicator(s) of the measuring device and given dietary contents level(s) for food according to the food selection information, a person can use the dietary system to facilitate easy use of the measuring device for measuring nutritional intake of a particular food. A user may determine the amount of food corresponding to the desired dietary contents level easily, i.e. reducing the effort and time necessary to keep track of the nutritional intake.

In one non-limiting example, the dietary system includes a display unit or component, such as an electronic display or print label, adapted to be carried on the measuring device for displaying the generated dietary correlation data that provides the reference between the measurement indicator(s) of the measuring device and given dietary contents level(s) for food according to the food selection information. In this manner, a person can use the dietary system to easily customize the measuring device for each particular food of interest. The customized measuring device displaying generated dietary correlation data for the particular food allows a person to measure nutritional intake of the particular food without measuring complications.

The dietary system can have a software system including a dietary application module which is stored in system storage/memory for execution by one or more processors to perform the mapping and thereby generate the dietary correlation data and optionally perform one or more other software processing methods of the embodiments described herein. The software system can include a kernel or operating system and a shell or interface. One or more application programs or modules, such as the dietary system application module, may be "loaded" (i.e. transferred from storage into memory for execution by the processor). The system receives user commands and data through user interface; these inputs may then be acted upon by the mapping processor, in accordance with instructions from operating module and/or application module.

The one or more processors executing the dietary application module can in one non-limiting example be a network server site connectable within a network which is the Internet, but equally can be any one of, combination of, or interconnection of, but not restricted to: a local area network (LAN); a wide area network (WAN): a home network; and a wireless network.

Note that the term "module" as used herein may refer to a collection of routines and data structures that perform a particular task or implements a particular abstract data type. Modules may be composed of two parts: 1) an interface that lists the constants, data types, variable, and routines that can be accessed by other modules or routines and 2) an implementation that is typically private, accessible only to that module, and includes source code that actually implements the routines in the module. The term "module" may also simply refer to an application, such as a computer program design, to assist in the performance of a specific task. In other examples, at least part of the modules may be implemented by hard-wired logic or other circuitry.

Reference will now be made to the drawings in which the various elements of embodiments will be given numerical designations and in which embodiments will be discussed so as to enable one skilled in the art to make and use the invention.

Specific reference to components, process steps, and other elements are not intended to be limiting. Further, it is understood that like parts bear the same reference numerals, when referring to alternate figures. It will be further noted that the figures are schematic and provided for guidance to the skilled reader and are not necessarily drawn to scale. Rather, the various drawing scales, aspect ratios, and numbers of components shown in the figures may be purposely distorted to make certain features or relationships easier to understand.

Referring to FIG. 1 of the accompany drawings, there is shown in a schematic block diagram an embodiment of the dietary measurement system 1 according to a first aspect of the present invention. The system 1 comprises a measuring device 2, which according to the present embodiment is a transparent measuring cup having an opening 3 on one axial end to receive food, such as for example nuts, fruit, cereals, crackers, sweets, fluid or any other desired food.

The measuring device 2 comprises five measurement indicators 4a-4e, which are represented by evenly spaced lines printed on the outer surface of the cup. Each of the measurement indicators 4a-4e is labeled with a unique identifier, e.g. as shown in FIG. 1 with the numerals 1-5. As will be apparent, each measurement indicator 4a-4e represents a defined and distinctive volume of the measuring device 2 when filled with food up to the desired indicator 4a-4e.

According to the present embodiment, each volume increment, i.e. the volume between the bottom of measuring device 2 and each further volume between two adjacent measurement indicators 4a-4e is equal. Thus, the increase in volume is linear, i.e. when the cup is filled up to measurement indicator 4b, the corresponding volume is twice the volume associated with measurement indicator 4a and so on, allowing an easy calculation of dietary correlation data, as will be discussed in the following. In other examples, the increase in volume may be non-linear.

The dietary measurement system 1 according to the present embodiment further comprises a mapping device 5 and a nutrition database 7. The mapping device 5 comprises an input interface 6, mapping processor 8 and an output device 9, such as a display, network communication or printing device. As indicated by the connecting lines in FIG. 1, the components of the mapping device 5 are connected with each other over suitable wired or wireless transmission links so that data may be sent and received as indicated. In one non-limiting embodiment, communication takes place over intermediate components and/or transmission links. Furthermore, it should be noted that more or other transmission links may be present; for example the connections between input interface 6, mapping processor 8 and output device 9 shown in FIG. 1 may be of duplex type for enhanced communication.

While the shown components of mapping device 5 may be formed integrally, such as in a common housing, it is nevertheless possible, that the components are provided in a distributed arrangement, as will be explained in the following with reference to further embodiments of the present aspect of the invention.

The input interface 6 according to the present embodiment is adapted to receive food selection information, a lower and an upper dietary contents level from user input. The food selection information comprises a selection of one or more food items from a list having multiple food items. The dietary contents level in the present embodiment comprises at least a calorie content level, such as e.g. 100 calories.

The nutrition database 7 comprises dietary contents information for food and more precisely according to the present embodiment, calorie content per volume increment associated with one of the measurement indicators 4a-4e. Since, as mentioned in the preceding, the volume increments associated with the measurement indicators 4a-4e are of equal volume, it is possible to determine the measurement indicator 4a-4e, correlating with the desired dietary contents level.

An example of the dietary contents information of nutrition database 7 is shown below (excerpt):

| Food | Caloric content [calories] per volume increment/measurement indicator |
|---|---|
| Dried apples | 10 |
| Dried cherries | 16 |
| Dried pineapples | 20 |
| Dried papaya | 14.3 |
| Figs | 12.5 |
| Peanuts | 50 |
| Raisins | 20 |
| Pistachios, shelled | 66.66 |
| Banana chips | 16.66 |
| ... | ... |
| ... | ... |
| ... | ... |

Certainly, the nutrition database 7 may comprise further information, such as content of nutrients, such as vitamins, protein, fat, carbohydrate, minerals, sodium, cholesterol.

The mapping device 5 further comprises the mapping processor 8 as mentioned before. The mapping processor 8 according to the present embodiment is a microprocessor having a suitable programming to receive the lower and upper dietary contents level and the food selection information from the input interface 6. Further, the mapping processor 8 is adapted to communicate with the nutrition database 7 and to generate dietary correlation data, which data provides a reference between the lower and upper dietary (caloric) contents levels and the measurement indicators on the measuring device 2 so that a user can easily determine the amount of food, corresponding to the desired caloric content.

The details of the operation of the dietary measurement system 1 according to FIG. 1 is explained in the following with reference to the flow diagram of FIG. 2.

In step 20, the input interface 6 receives the food selection information and the lower and an upper dietary (caloric) contents level from user input. For example, the user may have selected the following foods and dietary contents level:
Selected Food
Dried pineapples
Dried apples
Peanuts
Lower Dietary Contents Level:
50 calories
Upper Dietary Contents Level:
100 calories.

The received above information is then transmitted to the mapping processor 8 in step 21. Consequently in step 22, the mapping processor 8 queries the nutrition database 7 with regard to the selected food and according to the present example with "Dried papaya", "Dried apples" and "Peanuts". If the food is comprised in the dietary contents information, the database 7 in step 23 returns the caloric content information for the selected food items, i.e. here "20" for the item "Dried pineapples", "10" for the item "Dried apples" and "50" for the item "Peanuts". In case the food is not comprised in the dietary contents information of the database 7, an error message is transmitted to the mapping processor 8, e.g. "not found".

For each food item contained in the database 7, the mapping processor determines in step 24 dietary correlation data by dividing the lower and upper dietary contents levels by the determined dietary contents information, i.e.:
Dietary Correlation Data for Lower Dietary Contents Level:
Dried pineapples: 50 cal./20 cal. per meas. indicator=2.5
Dried apples: 50 cal./10 cal. per meas. indicator=5
Peanuts: 50 cal./50 cal. per meas. indicator=1
Dietary Correlation Data for Upper Dietary Contents Level:
Dried pineapples: 100 cal./20 cal. per meas. indicator=5
Dried apples: 100 cal./10 cal. per meas. indicator=10
Peanuts: 100 cal./50 cal. per meas. indicator=2

The determined dietary correlation data is then received by the output device 9 in step 25 to be provided to the user.

Accordingly, when the user then fills the measurement device 2 for example with dried pineapples up to measurement indicator "5" or 4e, the resulting amount of dried pineapples have a caloric content of 100 calories corresponding to the upper dietary contents level. For the lower dietary contents level, the user fills the measurement device 2 up to "2.5", i.e. a level equally spaced between measurement indicator "2" or 4b and measurement indicator "3" or 4c. Thus, the use of the measurement system 1 according to the present embodiment allows the user to easily keep track of his caloric intake.

Certainly, it should be noted that in the present example, the user would have to fill the measurement device 2 twice up to measurement indicator "5" or 4e to measure dried apples to the upper dietary contents level. However, the measurement device 2 may certainly have more or less volume than shown in FIG. 1 and a correspondingly higher or lower number of measurement indicators 4a-4e.

Furthermore, as already mentioned hereinbefore, in one non-limiting example the volume increments associated with the measurement indicators are non-linear. In such an example, the nutritional database can include Caloric content [calories] per each particular volume increment/measurement indicator and the mapping device can be configured to match the dietary content level to the particular indicator mostly closely corresponding to the dietary content level. In another example, the mapping processor applies a standard caloric content value, associated with the particular food and stored in the nutritional database, to an equation describing the non-linear volume increments to determine the measure indicator corresponding to the dietary content level.

As mentioned in the preceding, the output device 9 may be for example a display unit or a printing device to provide the user with the dietary correlation data. In a further embodiment, the mapping processor 8 may be adapted to generate a label printing template, such as a HTML or PDF file which then may be printed using an existing printing device of the user. In the latter case, the output device 9 would have the functionality of a network communication interface to send the template to the user. Some exemplary embodiments are discussed in more detail in the following.

Figure 3:
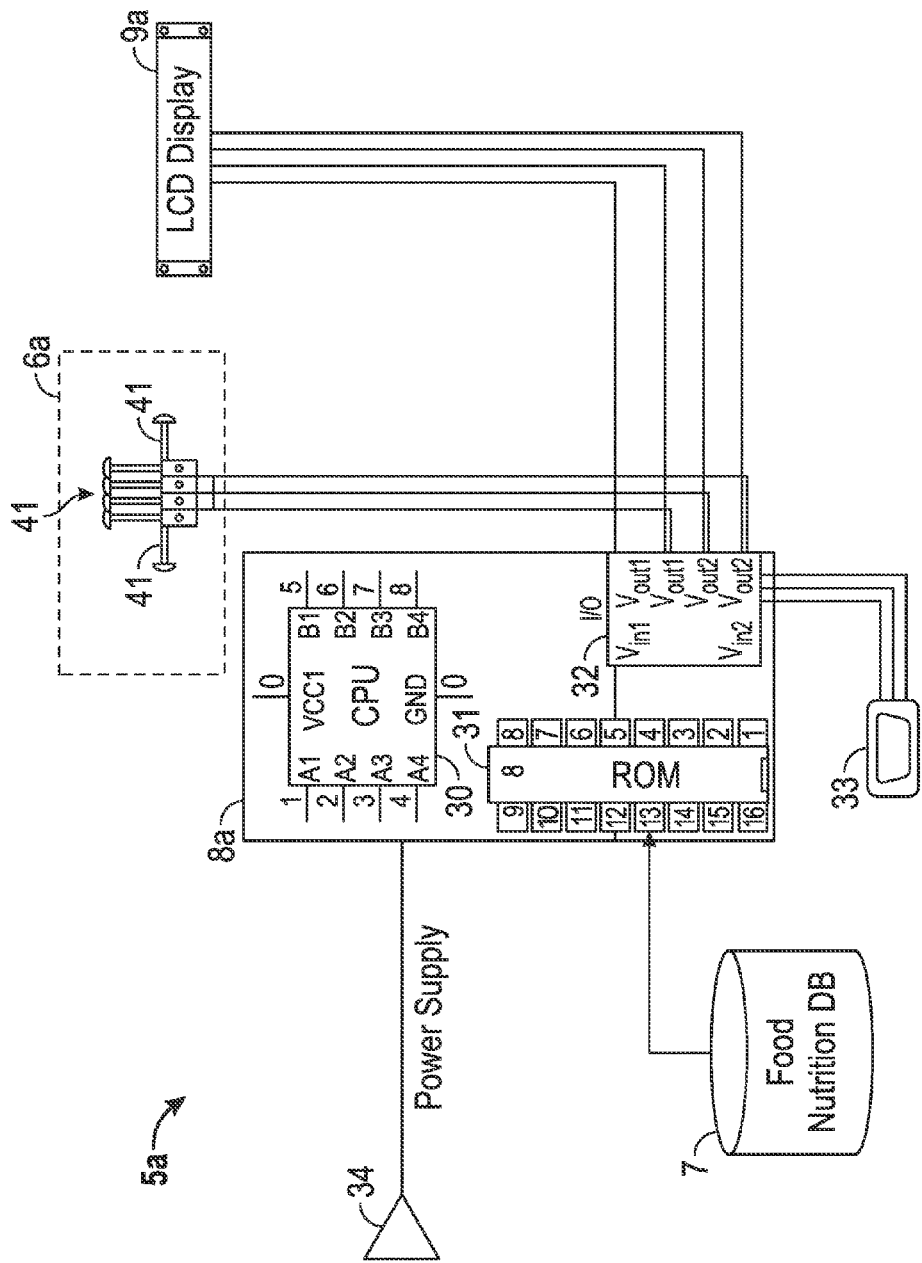
FIG. 3 shows an embodiment of a mapping device for use in a dietary measurement system in a schematic view.
Figure 4:
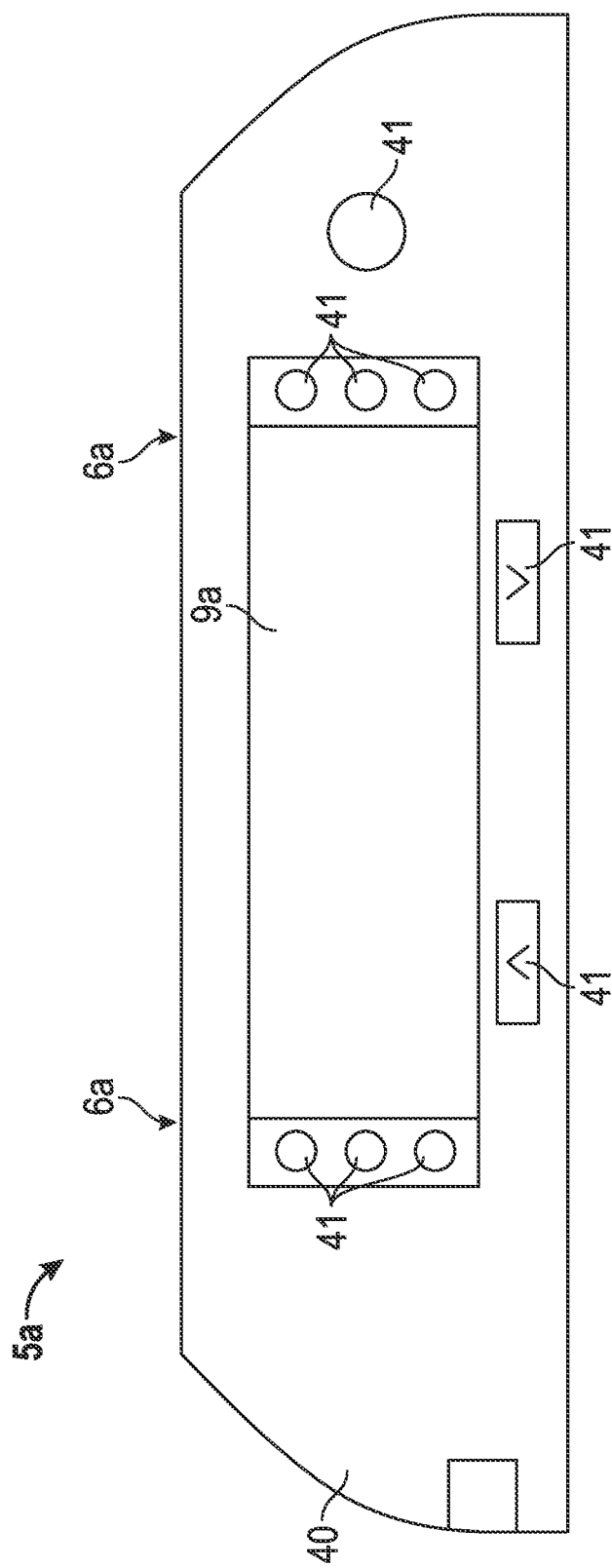
FIG. 4 shows a front view of the embodiment of FIG. 3, FIGS. 5 and 6 schematically illustrate a user interacting with the dietary measurement system according to the embodiment of FIGS. 3 and 4.

FIGS. 3 and 4 show an embodiment of the mapping device 5a for use in the dietary measurement system 1 in a schematic view. The mapping device 5a of FIGS. 3 and 4 is provided as a "stand alone" device, so that it can be used in an area of food preparation, i.e. the kitchen. The components of mapping device 5a are comprised in a housing 40 for a compact setup, as will become apparent from FIG. 4.

The general setup of the embodiment corresponds to FIG. 1. However, the input interface 6a in the present embodiment is a user interface having several buttons 41. The output device 9a according to the present embodiment is a LCD display, mounted in a front panel of the housing 40. Mapping processor 8a comprises a central processing unit (CPU) 30, a read-only memory device 31 comprising software to provide the operation explained above and a I/O-unit 32 for communication with the further components of mapping device 5a and the nutrition database 7. An external computer interface 33, such as a USB-interface, is provided to update the software and/or the dietary contents information of database 7. Electrical power is provided to the components of the mapping device 5a by a power connection 34, which according to the application, may be a connection to mains, e.g. using a suitable power supply, or a battery connection.

Figure 2:
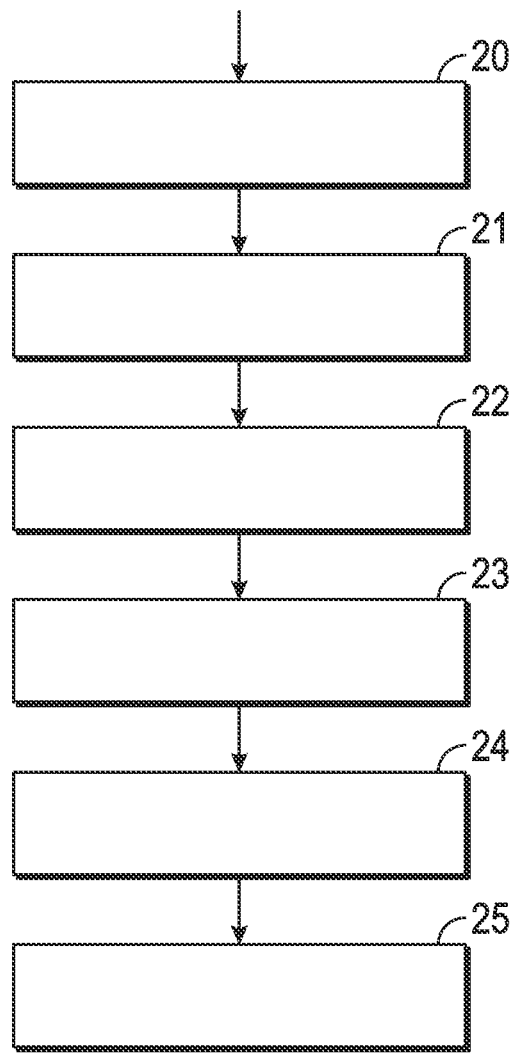
FIG. 2 illustrates the operation of the embodiment of FIG. 1 in a schematic flow diagram.

The operation of the embodiment of FIGS. 3 and 4 corresponds to the operation explained in the preceding with reference to FIG. 2 with the exception that the lower and upper dietary contents level are factory pre-set in CPU 30 and can be adjusted by a user over input interface 6a.

Figure 5:
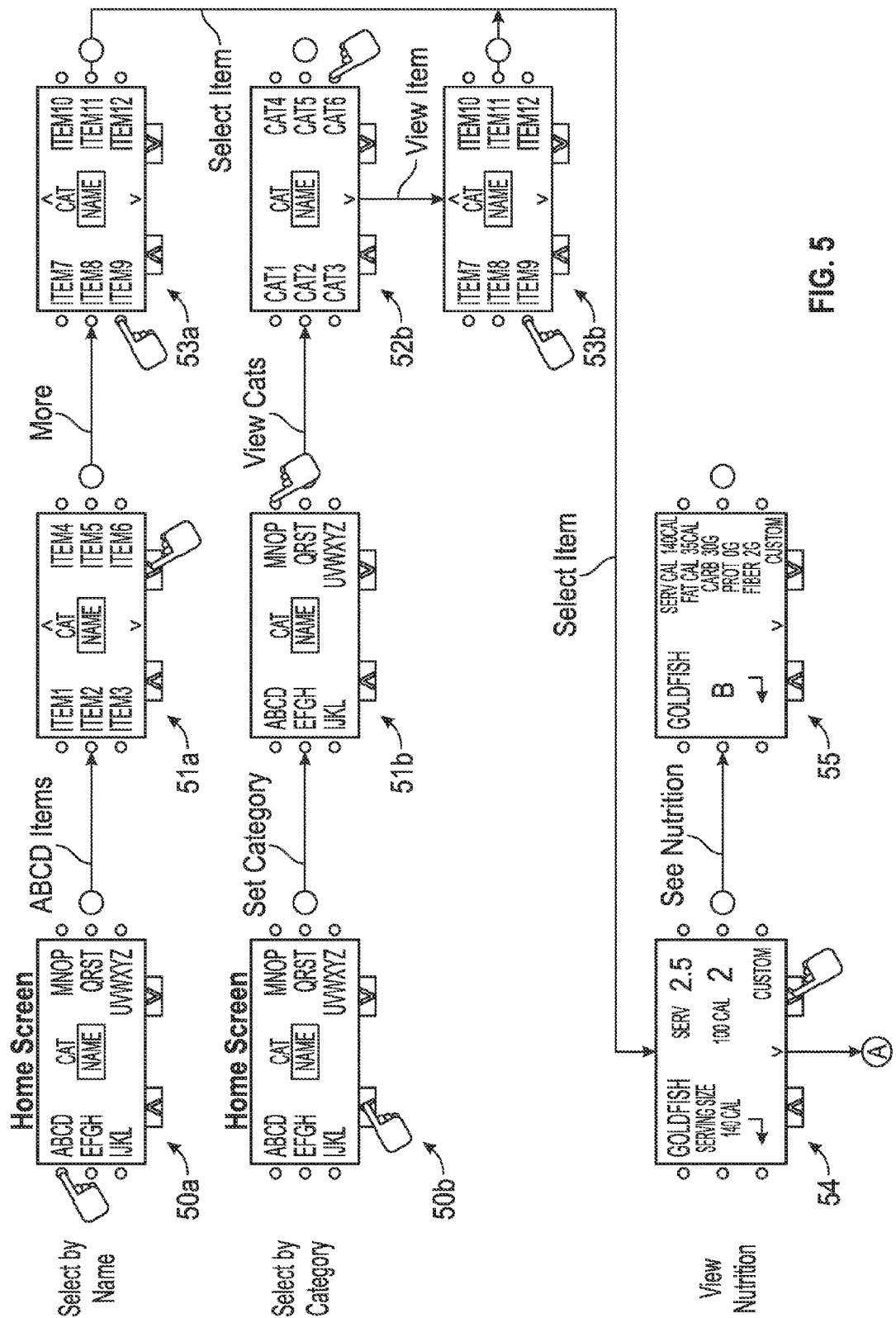
Figure 5:
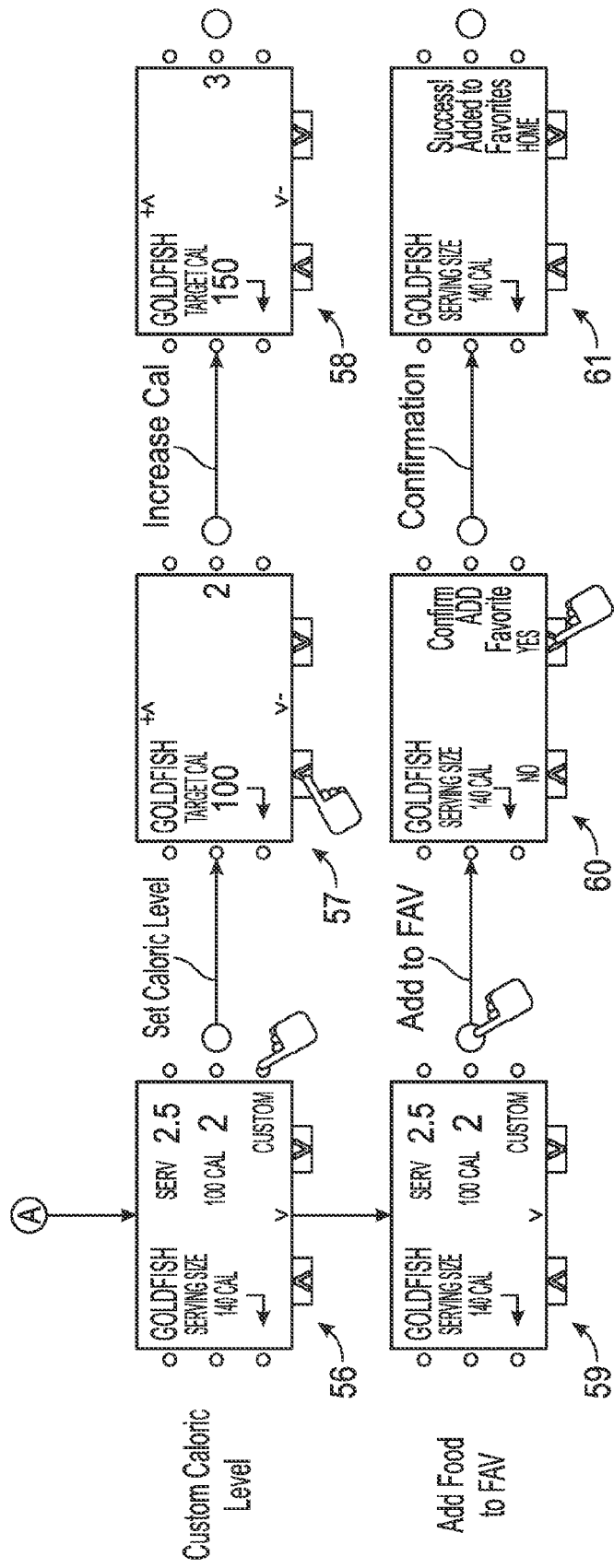
Figure 6:
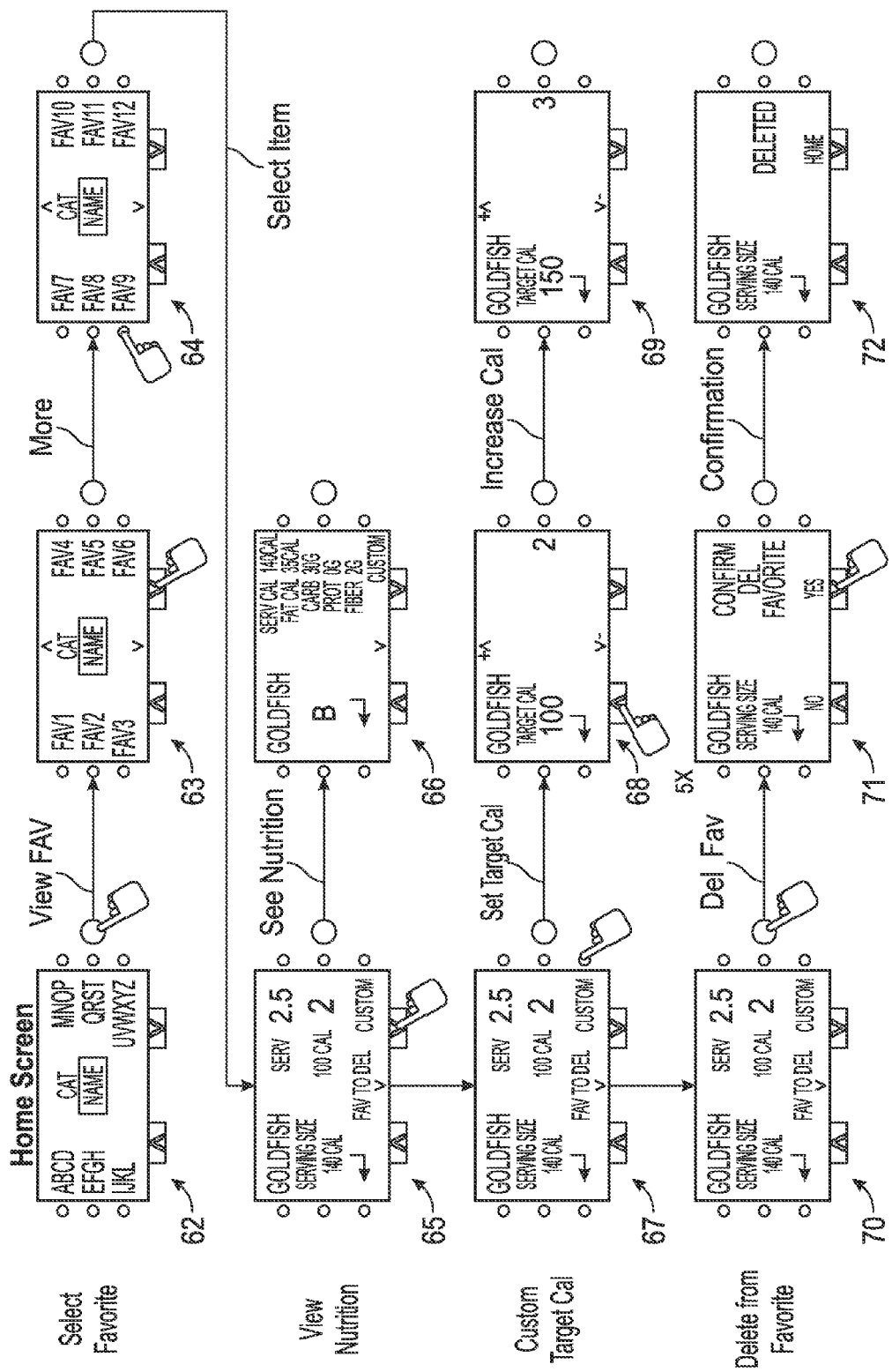

FIGS. 5 and 6 schematically illustrate a user operating the mapping device 5a together with the resulting display output according to the embodiment of FIGS. 3 and 4.

Corresponding to the embodiment discussed above, the user first selects the desired food. According to the present embodiment, the selection can be conducted by selecting the desired food from a list by name or by category.

When selecting the food by name, the process begins in step 50a by selecting the first letter of the desired food using one of the buttons 41 of input interface 6a. Upon selection, the mapping processor 8a queries the database 7 and then displays in step 51a on output device 9a all food according to the letter selected. The user may browse through different display pages using one of the buttons 41.

If the user likes to select the food by category, the process begins in step 50b by switching the display mode to category, indicated on the display by "CAT" being highlighted. The user then in step 51b selects a category by choosing the first letter of the respective category. After the mapping processor 8a queried the database 7 accordingly, the determined categories are displayed on output device 9a as shown in step 52b. The user may then select a category and all food of that category comprised in database 7 is displayed.

In both cases, the user may select the desired food in steps 53a and 53b, respectively. Assuming the user selects "ITEM 9" corresponding to the item "Goldfish crackers", the mapping processor 8a determines the dietary correlation data for this item, as discussed above with reference to FIG. 2. The resulting dietary correlation data is then displayed in step 54. The mapping processor 8a in this embodiment determines the dietary correlation data "2.5" for a "serving size" upper dietary contents level of 140 calories and "2" for a lower dietary contents level of 100 calories.

According to the present embodiment, the dietary contents information of nutrition database 7 further comprises additional information for the food, which are displayed to the user in step 55. Besides the caloric content, the total calories from fat and the total amount of carbohydrate, protein and fiber per 100 g are shown. Further food information can be accessed by the "V" button, which allows scrolling between display pages. The display of additional food information in step 55 can be personalized by pressing the "Custom" button. For example, the user may choose that instead of the fiber content, the sodium content is shown.

As mentioned before, the two dietary contents levels according to the present embodiment are factory pre-set. The user may however set a custom caloric contents level as shown in steps 56-58 of FIG. 5. To ease the selection of the users most favorite foods, the user may add the previously selected food to his favorites as shown in FIG. 5 with reference to steps 59-61.

The process of selecting food to display the dietary correlation information from a stored favorite is shown in FIG. 6 with reference to steps 62-66. Again, the user may also set a custom caloric contents level, as shown in steps 67-69. Finally, FIG. 6 shows with reference to steps 70-72 the process to remove a food item from the list of favorites.

As discussed in the preceding, the mapping device 5a according to the embodiment of FIGS. 3 and 4 is provided as a "stand alone" for use e.g. in the kitchen. According to the further embodiment of FIG. 7, the mapping device 5b may alternatively be a smart phone 70. In this embodiment, the input interface 6b and the output device 9b are formed integrally by a touch screen display 71, which serves for data entry and display. The mapping processor (not shown) may be formed by the processor of the smart phone together with software to provide the functionality explained above. Accordingly, the user may download a corresponding software package ("app") to his existing smart phone 70 to enable the device to provide the dietary correlation data.

Figure 7:
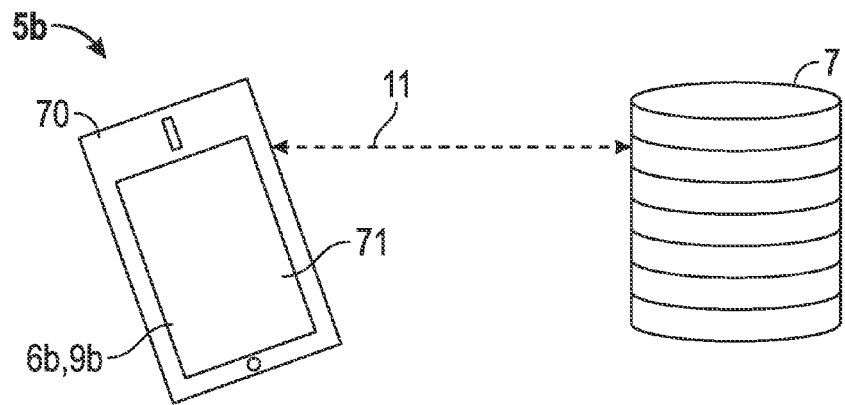
FIG. 7 shows a further embodiment of a mapping device for use in a dietary measurement system in a schematic view.

According to the present embodiment, the nutrition database 7 may be part of the downloaded software. Alternatively and as shown in FIG. 7, the nutrition database 7 may be provided separate from the smart phone 70 and connected to the mapping processor (not shown) using a suitable wired or wireless transmission link, e.g. over the Internet.

Figure 8:
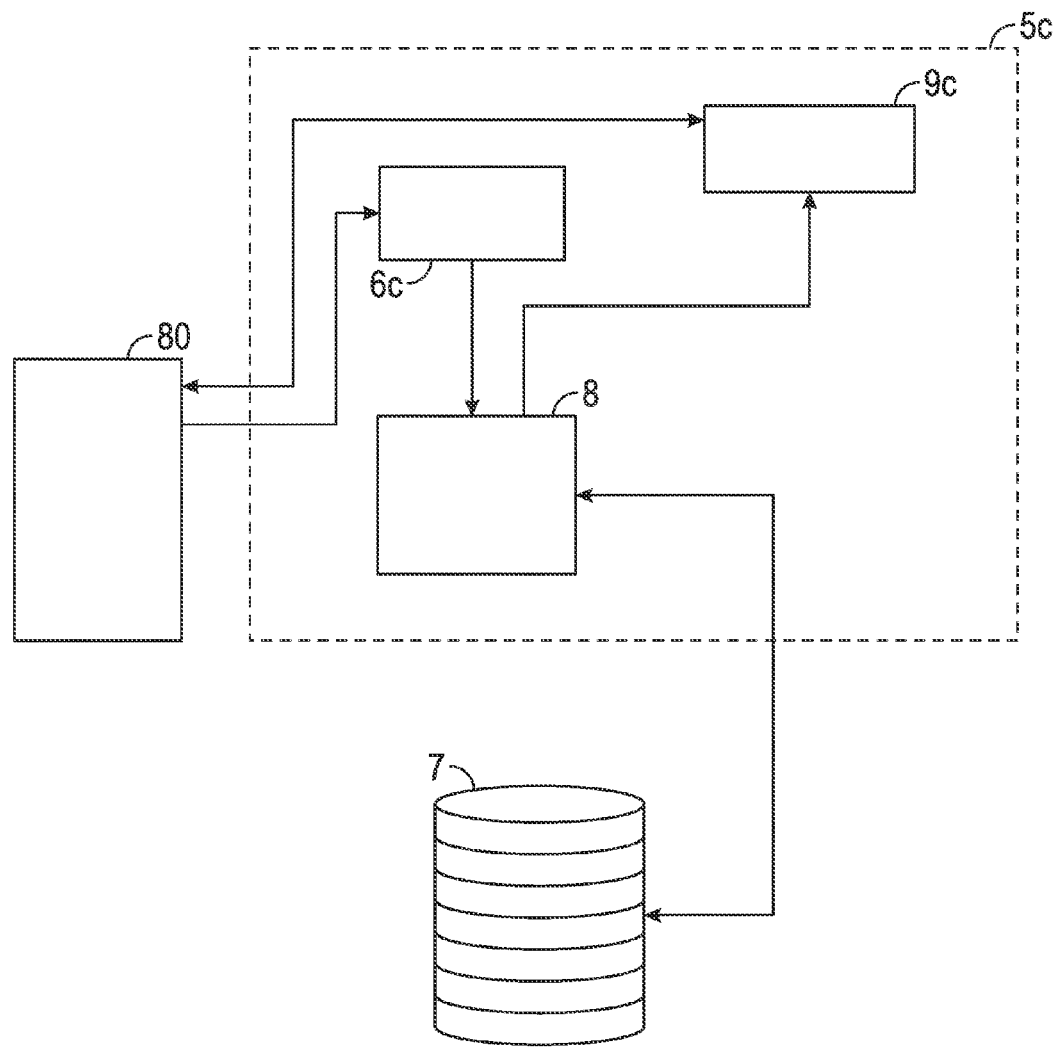
FIG. 8 shows another embodiment of a mapping device for use in a dietary measurement system in a schematic view.

FIG. 8 shows another embodiment of a mapping device 5c in a schematic view. The present embodiment corresponds to the embodiment shown in FIG. 1 with the exception that both, the input interface 6c and the output device 9c are configured to communicate with a computing device 80 of the user, e.g. over the Internet. The computing device 80 may be of any type, such as a desktop computer, laptop, tablet, hand held computer or also a smart phone.

According to the embodiment shown, the user may enter the food selection information, the lower and upper dietary content information on a website, provided by the input interface 6 or an intermediate (not shown) computing device and shown in the screen (not shown) of the user's computing device 80. Corresponding to the embodiment of FIG. 1, the mapping processor 8 determines the dietary content information. The dietary content information may be shown on the screen (not shown) of the user's computing device 80. Alternatively or additionally a label printing template may be generated by the mapping device 5c, such as a HTML- or PDF-file, which is then transferred to the user's computing device 80 using the output device 9c which is also connected to the Internet.

The label printing template according to the present embodiment comprises data, allowing a user's printing device (not shown) to print a dietary correlation label, i.e. a print-out comprising the generated dietary correlation data. For example, the label may comprise the following information based in the example discussed above:

| Food | Snack size: 50 calories | Serving size: 100 calories |
|---|---|---|
| Dried pineapples | 2.5 | 5 |
| Dried apples | 5 | 10 |
| Peanuts | 1 | 2 |
| ... | | |
| ... | | |
| ... | | |

Figure 9A:
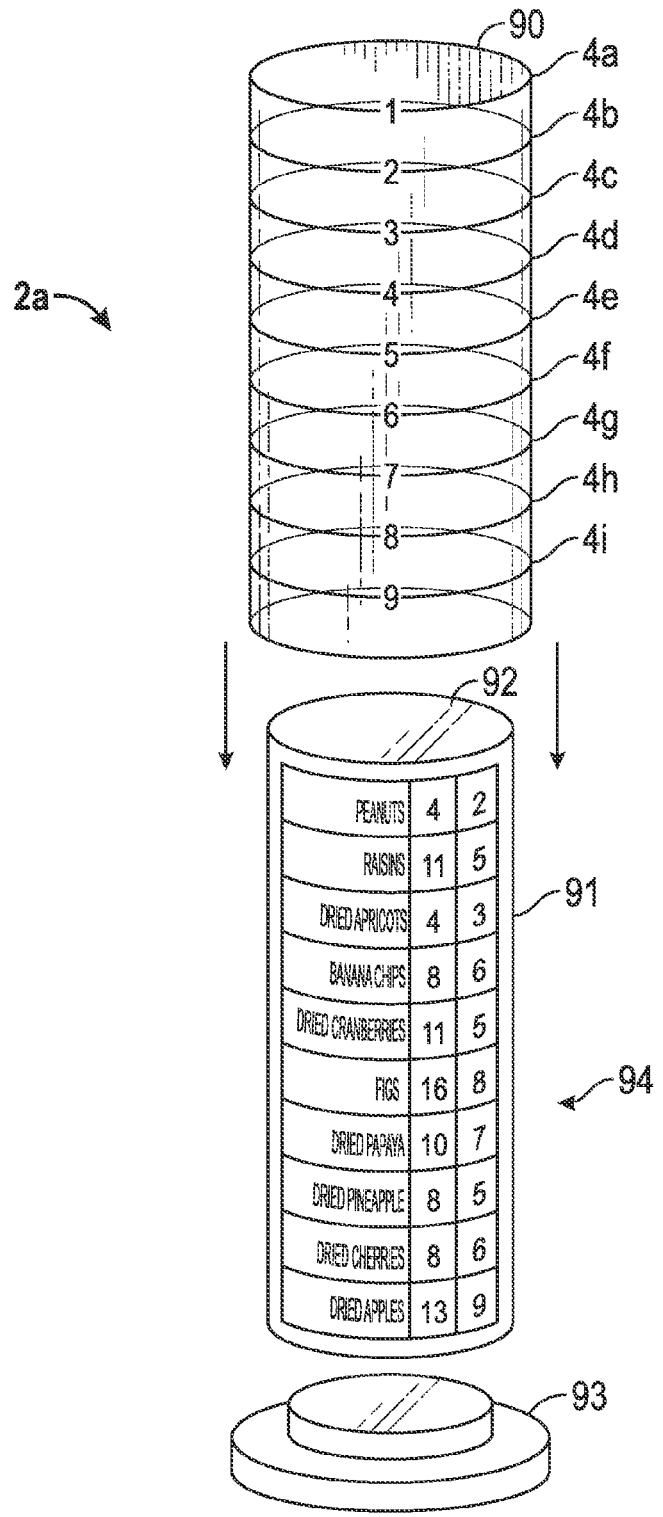
FIGS. 9a and 9b show an embodiment of a measuring device for use in a dietary measurement system in perspective views
Figure 9B:
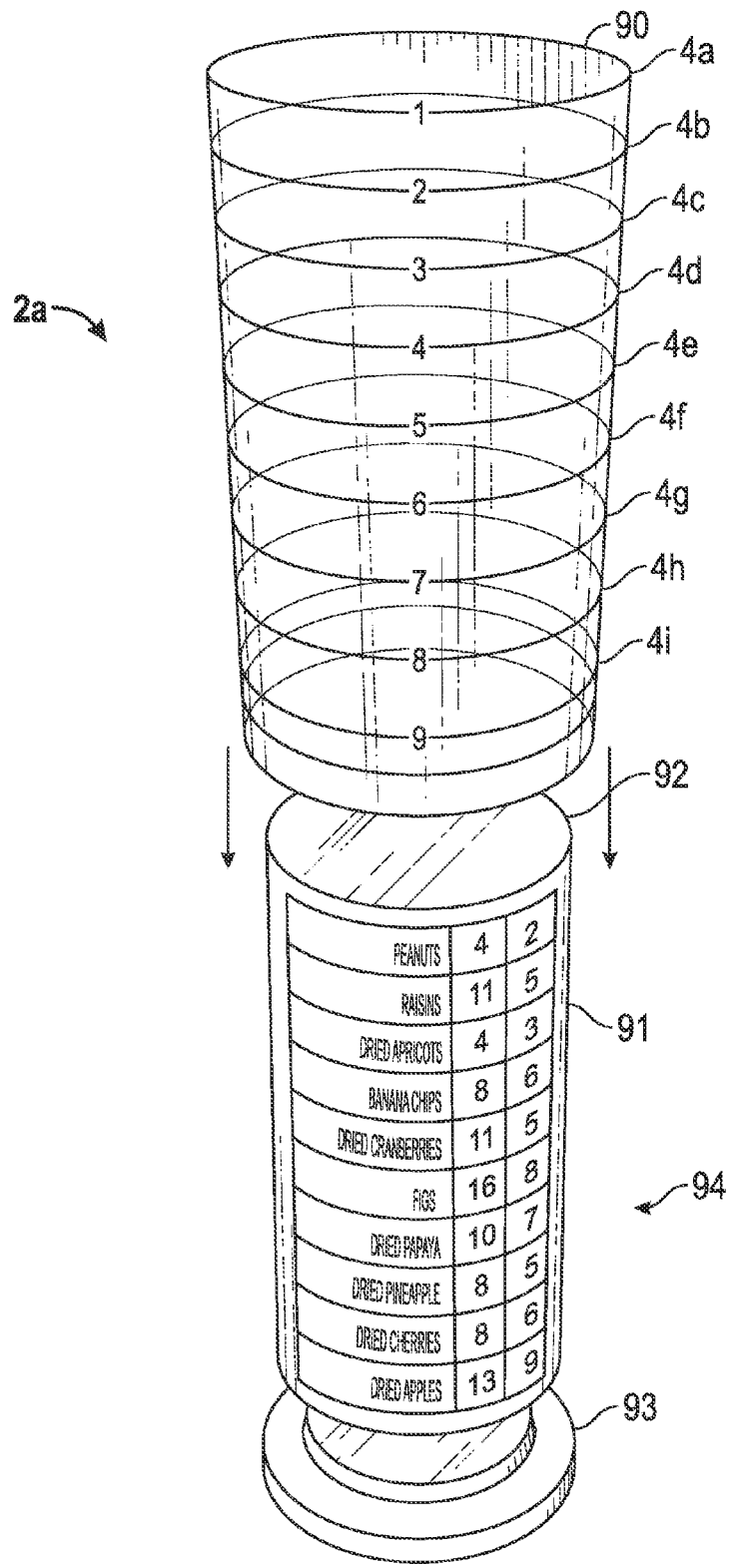

FIGS. 9a and 9b show a further embodiment of the measuring device 2a in exploded perspective views.

The measuring device 2a comprises an outer cylinder 90 and an inner cylinder 91, both made of transparent acrylic glass. The outer diameter of the inner cylinder 91 is slightly less than the inner diameter of the outer cylinder 90, so that the inner cylinder 91 may slide in the outer cylinder 90. The inner cylinder 91 comprises a sealing endplate 92 at one axial end, which provides that upon insertion of the inner cylinder 91 into the outer cylinder 90, a volume adjustable measuring compartment for food is formed between the walls of the outer cylinder 90 and the sealing endplate 92.

The cavity provided in the inner cylinder 91 forms a receptacle for the aforementioned dietary correlation label 94, which is shown placed in the receptacle in FIGS. 9a and 9b. A bottom cap 93 closes the receptacle and avoids unintended ejection of the dietary correlation label. The outer cylinder 90 comprises evenly spaced measurement indicators 4a-4i corresponding to the preceding discussion of the embodiment of FIG. 1.

Figure 10A:
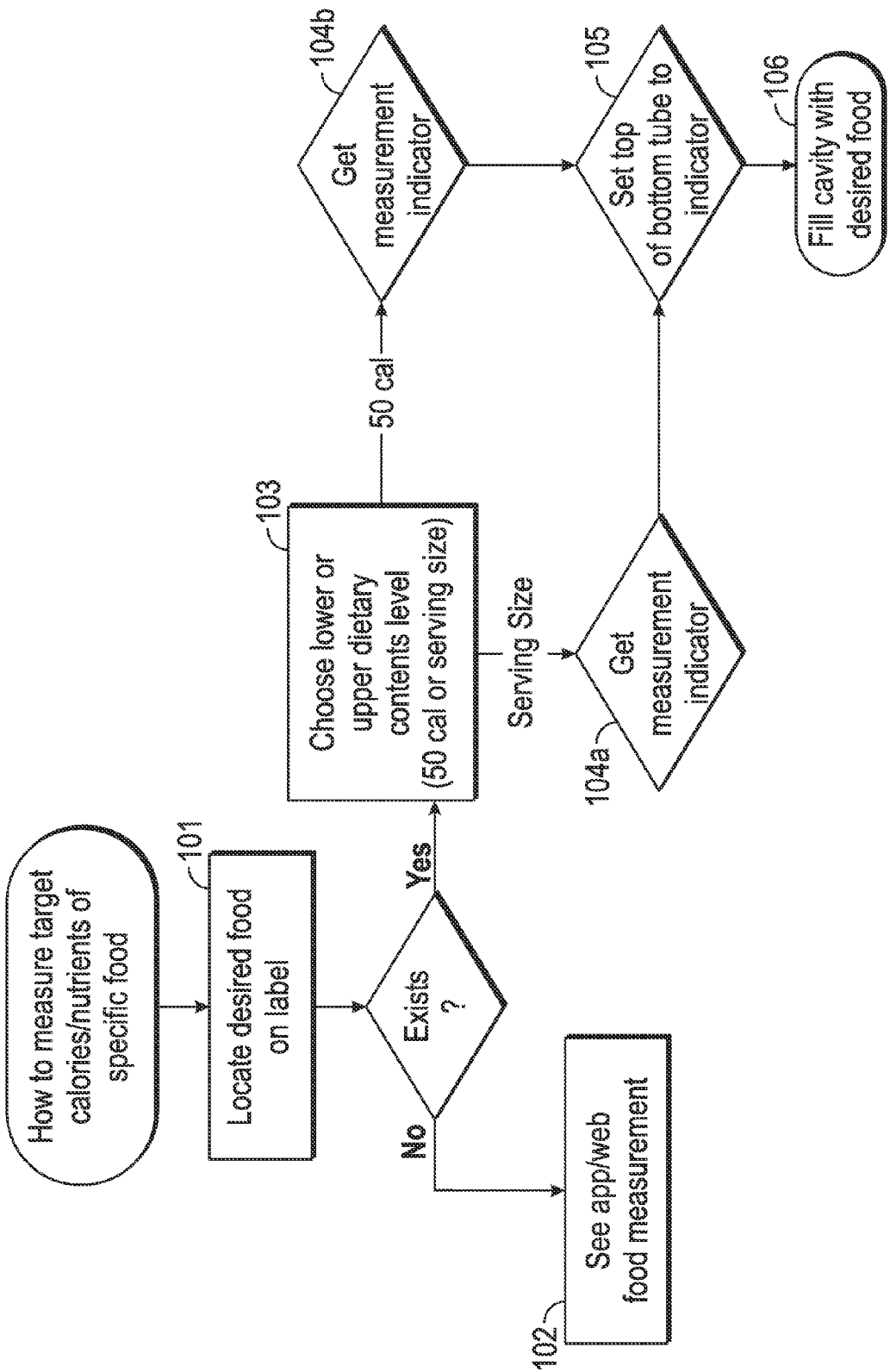
FIGS. 10a and 10b illustrate the operation of the embodiment of FIGS. 9a and 9b in schematic flow diagrams and FIG. 11 shows a further embodiment of a dietary measurement system combining the embodiment of a mapping device of FIGS. 3 and 4 and the embodiment of a measuring device according to FIGS. 9a and 9b.

For the dietary measurement using the measurement device 2a according to the present example, the user in one example determines the correct measurement indicator 4a-4i from the dietary correlation label, e.g. according to the flow chart shown in FIG. 10a. First, the user starts locating the desired food on the label in step 101.

If the desired food does not exist, various possibilities exist. For example, the user may in step 102 and corresponding to FIG. 8 query the website to display the dietary correlation data for the desired food or to generate a new dietary correlation label comprising the desired food. Alternatively or additionally, the user may in step 102 refer to the "app" on his smart phone 70, as explained with reference to FIG. 7.

In case the desired food exists, e.g. in the example above "dried pineapples", the user selects the desired lower or upper dietary contents level in step 103 and determines the correct measurement indicator 4a-4i in steps 104a and 104b.

According to the above, the label indicates "5" for a serving size of dried pineapples. Then, the user in step 105 slides the inner cylinder 91 in the outer cylinder 90 until the sealing endplate 92 of the inner cylinder 91 aligns with the correct measurement indicator, i.e. the indicator 4e labeled with "5".

When the user now fills the measuring compartment with the desired dried pineapples up to the upper end of outer cylinder 90 in step 106, the resulting amount of dried pineapples corresponds to 100 calories.

Alternatively or additionally to the use of the dietary correlation label, the user may employ the measuring device 2a according to FIGS. 9a and 9b with an "app", i.e. a software package as explained with reference to FIG. 7 or a website as explained in connection with FIG. 8. As mentioned in the preceding this may for example be necessary in case the desired food is not on the dietary correlation label the user has printed.

Figure 10B:
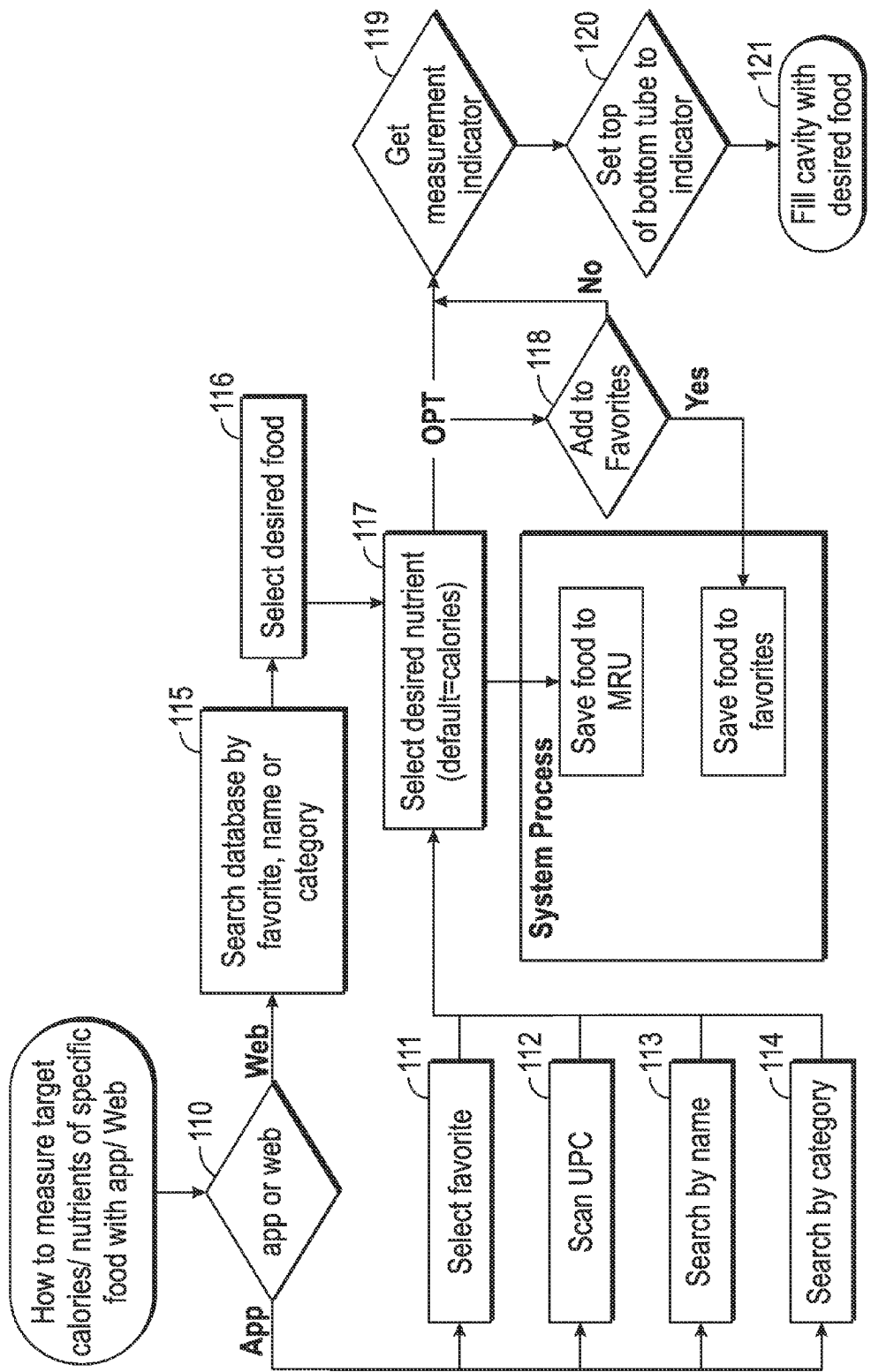

The operation of the user employing the "app" according to FIG. 7 or the web service according to FIG. 8 is in the following explained with reference to the flow chart of FIG. 10b. For reasons of clarity, both procedures are shown in the same flow chart beginning with step 110, although it is certainly not necessary but possible that the user accesses both, the "app" and the website.

In the example of the usage of the "app", e.g. with smart phone 70 according to FIG. 7, the user may select the desired food from a list of favorite foods in step 111, by searching by name or category according to steps 113 and 114 or by scanning the UPC (universal product code) in step 112. In the latter case, the smart phone 70 should be equipped with a camera or with another type of product and/or bar code scanner.

Alternatively, when using the mentioned web service, the user may search the database by name, category or prior selected favorites in step 115 and subsequently select the desired food in step 116.

In both cases, the user may then in step 117 optionally select the desired nutrient, i.e. the desired dietary content level(s). As mentioned in the preceding, the dietary contents level typically comprises the calorie content level, but the user may certainly select a different dietary contents level. For example, in case the user is interested in keeping track of his sodium intake, he may select a sodium content level. In this case, the dietary contents information stored in nutrition database 7 would comprise sodium contents information.

Once the dietary content level(s) are set for the desired food, the user may optionally choose to have the food and/or dietary contents level(s) saved to his favorites in step 118. The measurement indicator, corresponding to the set dietary contents level is then shown to the user in step 119 to allow the user to set the measurement device 2a accordingly to the determined measurement indicator.

Also in this example, the user would then slide the inner cylinder 91 of measurement device 2a in the outer cylinder 90 until the sealing endplate 92 of the inner cylinder 91 aligns with the correct measurement indicator in step 120.

When the user now fills the measuring compartment with the desired food up to the upper end of outer cylinder 90 in step 121, the resulting amount of food corresponds to the desired dietary contents level.

Figure 11:
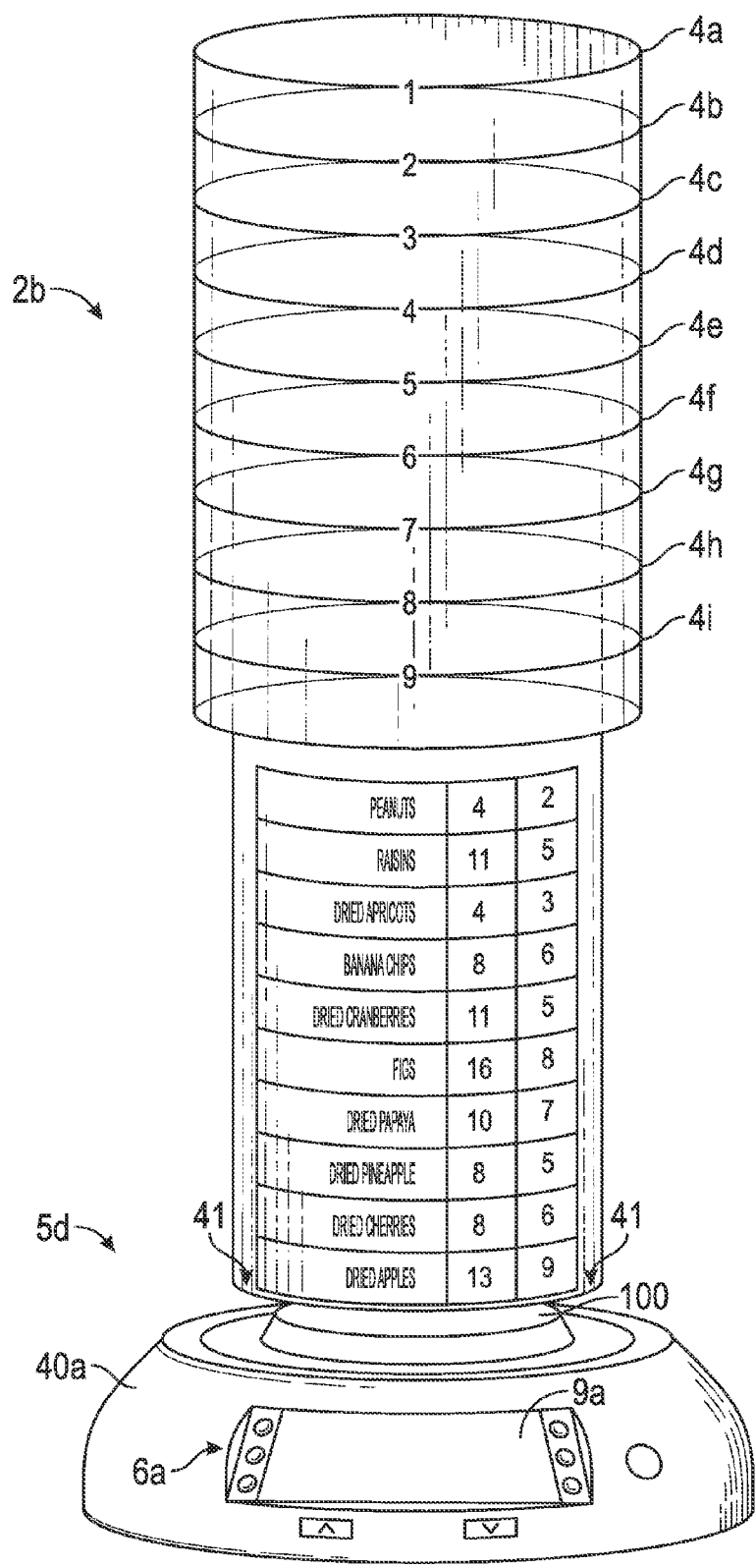

FIG. 11 shows a further embodiment of a dietary measurement system. In the present embodiment, the mapping device 5d corresponds to the setup of FIGS. 3 and 4 with the exception that the top portion 100 of the housing 40a is adapted for a removable engagement with the inner cylinder 91 of the measuring device 2b. The measuring device 2b corresponds to the embodiment of FIGS. 9a and 9b with the exception that the bottom cap 93 is omitted.

The present embodiment allows to easily use and store both the mapping device 5d and the measurement device 2b together, e.g. on a kitchen countertop.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein
- in the embodiments described in the preceding, the nutrition database 7 is formed integrally with the mapping device 5,
- in the embodiments of FIG. 1 or 8, the input interface 6/6c is formed integrally with the output device 9/9c,
- in the embodiment of FIG. 7, instead of a smart phone, a tablet, notebook or desktop computer is used and/or
- in the embodiment of FIG. 8, instead to providing a label template, dietary correlation data is displayed on a screen (not shown) of the users' computing device 80.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims.

The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A dietary measurement system with at least
    a measuring device adapted to accommodate food having multiple measurement indicators representing defined volumes, wherein said measuring device comprises a measuring compartment to accommodate food and a receptacle for receiving a dietary correlation label, said receptacle being arranged so that said dietary correlation label is separated from said food;
    a nutrition database comprising dietary contents information for food and
    a mapping device, comprising
        an input interface for receiving food selection information and
        a mapping processor, connected with said input interface and said nutrition database, said mapping processor being adapted to generate dietary correlation data from said dietary contents information, said dietary correlation data providing a reference between one of said measurement indicators of said measuring device and a given dietary contents level for food according to said food selection information.

2. The dietary measurement system according to claim 1, wherein said input interface is adapted to receive at least a lower dietary contents level and an upper dietary contents level and said mapping processor is adapted to generate dietary correlation data for both of said dietary contents levels.

3. The dietary measurement system according to claim 1, wherein said dietary contents level comprises at least a caloric content level.

4. The dietary measurement system according to claim 1, wherein said dietary contents information comprises at least caloric content information.

5. The dietary measurement system according to claim 1, wherein said mapping device further comprises an output device, connected with said mapping processor.

6. The dietary measurement system according to claim 5, wherein said output device comprises a display unit to display said dietary correlation data.

7. The dietary measurement system according to claim 1, wherein said mapping device comprises a housing, said housing having a connecting portion for removable fixation of said mapping device to the measuring device.

8. The dietary measurement system according to claim 1, wherein said mapping device is further adapted to generate a label printing template comprising said dietary correlation data to allow printing of a dietary correlation label.

9. The dietary measurement system according to claim 8, wherein said output device comprises a printing device to provide said dietary correlation label from said label printing template.

10. The dietary measurement system according to claim 1, wherein said measuring compartment is a volume adjustable compartment.

11. The dietary measurement system according to claim 1, wherein said measuring device further comprises an outer and an inner cylinder, said inner cylinder being arranged slidable in said outer cylinder.

12. The dietary measurement system according to claim 11, wherein said inner cylinder comprises at least a sealing endplate on a first axial end of said inner cylinder, so that said measuring compartment is formed between said outer cylinder and said endplate.

13. The dietary measurement system according to claim 12, wherein said receptacle is formed in said inner cylinder.

14. A computer-readable medium including contents that are configured to cause a computing system to correlate dietary information to a defined volume of a measuring device adapted to accommodate food having multiple measurement indicators by performing a method comprising:
   receiving food selection information,
   receiving dietary contents information according said food selection information, and
   generating dietary correlation data from said dietary information, said dietary correlation data providing a reference between one of said measurement indicators and a given dietary contents level for food according to said food selection information; and
   further comprising generating a label printing template, said label printing template comprising said dietary correlation data to allow printing of a dietary correlation label.

* * * * *